United States Patent [19]
Scaglioni et al.

[11] Patent Number: 6,060,595
[45] Date of Patent: May 9, 2000

[54] INHIBITION OF VIRAL REPLICATION

[75] Inventors: Pier Paolo Scaglioni; Margherita Melegari, both of Boston; Jack R. Wands, Wahan, all of Mass.

[73] Assignee: The General Hospital Corporation, Boston, Mass.

[21] Appl. No.: 08/968,747

[22] Filed: Sep. 3, 1997

Related U.S. Application Data

[60] Provisional application No. 60/025,370, Sep. 3, 1996.

[51] Int. Cl.⁷ .................................................. C07H 21/04
[52] U.S. Cl. ........................................................ 536/23.72
[58] Field of Search .................................. 536/23.1, 23.4, 536/23.72

[56] References Cited

FOREIGN PATENT DOCUMENTS

WO 88/05469  7/1988  WIPO .
WO 89/01518  2/1989  WIPO .

OTHER PUBLICATIONS

Birnbaum et al., "Hepatitis B Virus Nucleocapsid Assembly: Primary Structure Requirements in the Core Protein", Journal of Virology 64:3319–3330, 1990.

Hatton et al., "RNA–and DNA–Binding Activities in Hepatitis B Virus Capsid Protein: A Model for Their Roles in Viral Replication", Jounral of Virology 66:5232–5241, 1992.

Nassal, Michael, "The Arginine–Rich Domain of the Hepatitis B Virus Core Protein Is Required for Pregenome Encapsidation . . . ", Journal of Virology 66:4107–4116, 1992.

Scaglioni et al., "Characterization of Hepatitis B Virus Core Mutants That Inhibit Viral Replication", Virology 205:112–120, 1994.

Zhou et al., "Characterization of Hepatitis B Virus Capsid Particle Assembly in Xenopus Oocytes", Journal of Virology 66:3086–3092, 1992.

*Primary Examiner*—Donna C. Wortman
*Assistant Examiner*—Brenda G. Brumback
*Attorney, Agent, or Firm*—Fish & Richardson P.C.

[57] ABSTRACT

The invention relates to methods and compositions for inhibition of viral replication in animal cells. In particular, inhibition of viral replication in a target cell is achieved by introducing into the cell (1) a protein which can be incorporated along with wild type nucleocapsid subunits into a viral nucleocapsid assembling within the cell, and thereby renders the nucleocapsid deficient in encapsidating viral nucleic acid; or (2) a recombinant nucleic acid construct that directs overexpression of the protein.

10 Claims, 2 Drawing Sheets

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 154 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:1:

```
Ser Lys Leu Cys Leu Gly Trp Leu Trp Gly Met Asp Ile Asp Pro Tyr
1               5                   10                  15

Lys Glu Phe Gly Ala Thr Val Glu Leu Leu Ser Phe Leu Pro Ser Asp
                20                  25                  30

Phe Phe Pro Ser Val Arg Asp Leu Leu Asp Thr Ala Ser Ala Leu Tyr
            35                  40                  45

Arg Glu Ala Leu Glu Ser Pro Glu His Cys Ser Pro His His Thr Ala
50                  55                  60

Leu Arg Gln Ala Ile Leu Cys Trp Gly Glu Leu Met Thr Leu Ala Thr
65                  70                  75                  80

Trp Val Gly Val Asn Leu Glu Asp Pro Ala Ser Arg Asp Leu Val Val
                85                  90                  95

Ser Tyr Val Asn Thr Asn Met Gly Leu Lys Phe Arg Gln Leu Leu Trp
                100                 105                 110

Phe His Ile Ser Cys Leu Thr Phe Gly Arg Glu Thr Val Ile Glu Tyr
            115                 120                 125

Leu Val Ser Phe Gly Val Trp Ile Arg Thr Pro Pro Ala Tyr Arg Pro
        130                 135                 140

Pro Asn Ala Pro Ile Leu Ser Thr Leu Pro
145                 150
```

(2) INFORMATION FOR SEQ ID NO:2:

(i) SEQUENCE CHARACTERISTICS:
        (A) LENGTH: 193 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:2:

```
Ser Lys Leu Cys Leu Gly Trp Leu Trp Gly Met Asp Ile Asp Pro Tyr
1               5                   10                  15

Lys Glu Phe Gly Ala Thr Val Glu Leu Leu Ser Phe Leu Pro Ser Asp
                20                  25                  30

Phe Phe Pro Ser Val Arg Asp Leu Leu Asp Thr Ala Ser Ala Leu Tyr
            35                  40                  45

Arg Glu Ala Leu Glu Ser Pro Glu His Cys Ser Pro His His Thr Ala
    50                  55                  60

Leu Arg Gln Ala Ile Leu Cys Trp Gly Glu Leu Met Thr Leu Ala Thr
65                  70                  75                  80

Trp Val Gly Val Asn Leu Glu Asp Pro Ala Ser Arg Asp Leu Val Val
```

```
              85                  90                  95
Ser Tyr Val Asp Thr Asn Met Gly Leu Lys Phe Arg Gln Leu Leu Trp
               100                 105                 110

Phe Met Ile Ser Cys Leu Thr Phe Gly Arg Glu Thr Val Ile Glu Tyr
               115                 120                 125

Leu Val Ser Phe Gly Val Trp Ile Arg Thr Pro Pro Ala Tyr Arg Pro
               130                 135                 140

Pro Asn Ala Pro Ile Leu Ser Thr Leu Pro Glu Thr Val Val Arg
145                150                 155                 160

Arg Arg Gly Arg Ser Pro Arg Arg Thr Pro Ser Pro Arg Arg Arg
               165                 170                 175

Arg Ser Gln Ser Pro Arg Arg Arg Ser Gln Ser Arg Glu Ser Gln
               180                 185                 190

Cys
```

(2) INFORMATION FOR SEQ ID NO:3:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:3:

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
               20                  25                  30

Asp Pro Tyr Lys Glu Phe Gly Ala Thr Val Glu Leu Leu Ser Phe Leu
               35                  40                  45

Pro Ser Asp Phe Phe Pro Ser Val Arg Asp Leu Leu Asp Thr Ala Ser
           50                  55                  60

Ala Leu Tyr Arg Glu Ala Leu Glu Ser Pro Glu His Cys Ser Pro His
65              70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
               100                 105                 110

Leu Val Val Ser Tyr Val Asn Thr Asn Met Gly Leu Lys Phe Arg Gln
               115                 120                 125

Leu Leu Trp Phe His Ile Ser Cys Leu Thr Phe Gly Arg Glu Thr Val
               130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
               165                 170                 175

Val Val Arg Arg Arg Gly Arg Ser Pro Arg Arg Arg Thr Pro Ser Pro
               180                 185                 190

Arg Arg Arg Arg Ser Gln Ser Pro Arg Arg Arg Arg Ser Gln Ser Arg
               195                 200                 205

Glu Ser Gln Cys
210
```

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:4:

Asp Tyr Lys Asp Asp Asp Asp Lys Ser
1               5

(2) INFORMATION FOR SEQ ID NO:5:

(i) SEQUENCE CHARACTERISTICS:
            (A) LENGTH: 39 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:5:

Glu Thr Thr Val Val Arg Arg Arg Gly Arg Ser Pro Arg Arg Arg Thr
1               5                   10                  15

Pro Ser Pro Arg Arg Arg Arg Ser Gln Ser Pro Arg Arg Arg Arg Ser
                20                  25                  30

Gln Ser Arg Glu Ser Gln Cys
        35

(2) INFORMATION FOR SEQ ID NO:6:

(i) SEQUENCE CHARACTERISTICS:
            (A) LENGTH: 19 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:6:

Met Gln Leu Phe Asn Leu Cys Leu Ile Ile Ser Cys Ser Cys Pro Thr
1               5                   10                  15

Val Gln Ala (2) INFORMATION FOR SEQ ID NO:7:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:7:

Gly Ala Pro Val Pro Tyr Asp Pro Leu Glu Pro Arg
1               5                   10

(2) INFORMATION FOR SEQ ID NO:8:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:8:

Glu Gln Lys Leu Ile Ser Glu Glu Asp Leu Asn
1               5                   10

(2) INFORMATION FOR SEQ ID NO:9:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:9:

Tyr Thr Asp Ile Glu Met Asn Arg Leu Gly Lys
1               5                   10

(2) INFORMATION FOR SEQ ID NO:10:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:10:

Ala Ser Met Thr Gly Gly Gln Gln Met Gly Arg
1               5                   10

(2) INFORMATION FOR SEQ ID NO:11:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:11:

Gln Pro Glu Leu Ala Pro Glu Asp Pro Glu Asp
1               5                   10

(2) INFORMATION FOR SEQ ID NO:12:

(i) SEQUENCE CHARACTERISTICS:
            (A) LENGTH: 9 amino acids
            (B) TYPE: amino acid
            (C) STRANDEDNESS: Not Relevant
            (D) TOPOLOGY: linear (ii) MOLECULE TYPE: protein (xi) SEQUENCE DESCRIPTION: SEQ ID NO:12:

Tyr Pro Tyr Asp Val Pro Asp Tyr Ala
1               5

(2) INFORMATION FOR SEQ ID NO:13:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:13:

CGGGGTACCA TGTCCAAGCT GTGCCTTGGG TG                32

(2) INFORMATION FOR SEQ ID NO:14:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:14:

GCTCTAGACT TGTCATCGTC GTCCTTGTAA TCTTCCAAAT TAACACCCAC CCAGG       55

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

Ala Gly Asp Tyr Cys Cys
1               5

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

Asp Pro Ala Ser
1

(2) INFORMATION FOR SEQ ID NO:17:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

Met Ser Lys Leu Cys Leu Gly Trp Leu Trp Gly Met Asp Ile Asp Pro
1               5                   10                  15

Tyr Lys Glu Phe Gly Ala Thr Val Glu Leu Leu Ser Phe Leu Pro Ser
                20                  25                  30

Asp Phe Phe Pro Ser Val Arg Asp Leu Leu Asp Thr Ala Ser Ala Leu
            35                  40                  45

Tyr Arg Glu Ala Leu Glu Ser Pro Glu His Cys Ser Pro His His Thr
        50                  55                  60

Ala Leu Arg Gln Ala Ile Leu Cys Trp Gly Glu Leu Met Thr Leu Ala
65                  70                  75                  80

Thr Trp Val Gly Val Asn Leu Glu Asp Pro Ala Ser Arg Asp Leu Val
                85                  90                  95

```
Val Ser Tyr Val Asn Thr Asn Met Gly Leu Lys Phe Arg Gln Leu Leu
            100                 105                 110

Trp Phe His Ile Ser Cys Leu Thr Phe Gly Arg Glu Thr Val Ile Glu
            115                 120                 125

Tyr Leu Val Ser Phe Gly Val Trp Ile Arg Thr Pro Pro Ala Tyr Arg
            130                 135             140

Pro Pro Asn Ala Pro Ile Leu Ser Thr Leu Pro
145                 150                 155
```

(2) INFORMATION FOR SEQ ID NO:18:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ser Lys Leu Cys Leu Gly Trp Leu Trp Gly Met Asp Ile Asp Pro
1               5                   10                  15

Tyr Lys Glu Phe Gly Ala Thr Val Glu Leu Leu Ser Phe Leu Pro Ser
            20                  25                  30

Asp Phe Pro Ser Val Arg Asp Leu Leu Asp Thr Ala Ser Ala Leu
            35                  40                  45

Tyr Arg Glu Ala Leu Glu Ser Pro Glu His Cys Ser Pro His His Thr
        50                  55                  60

Ala Leu Arg Gln Ala Ile Leu Cys Trp Gly Glu Leu Met Thr Leu Ala
65                  70                  75                  80

Thr Trp Val Gly Val Asn Leu Glu Asp Pro Ala Ser Arg Asp Leu Val
                85                  90                  95

Val Ser Tyr Val Asn Thr Asn Met Gly Leu Lys Phe Arg Gln Leu Leu
            100                 105                 110

Trp Phe His Ile Ser Cys Leu Thr Phe Gly Arg Glu Thr Val Ile Glu
            115                 120                 125

Tyr Leu Val Ser Phe Gly Val Trp Ile Arg Thr Pro Pro Ala Tyr Arg
            130                 135             140

Pro Pro Asn Ala Pro Ile Leu Ser Thr Leu Pro Glu Thr Thr Val Val
145                 150                 155                 160

Arg Arg Arg Gly Arg Ser Pro Arg Arg Thr Pro Ser Pro Arg Arg
                165                 170                 175

Arg Arg Ser Gln Ser Pro Arg Arg Arg Ser Gln Ser Arg Glu Ser
            180                 185                 190

Gln Cys
```

(2) INFORMATION FOR SEQ ID NO:19:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:19:

```
Met Ser Lys Leu Cys Leu Gly Trp Leu Trp Gly Met Asp Ile Asp Pro
1               5                   10                  15

Tyr Lys Glu Phe Gly Ala Thr Val Glu Leu Leu Ser Phe Leu Pro Ser
```

```
                    20                  25                  30
Asp Phe Phe Pro Ser Val Arg Asp Leu Leu Asp Thr Ala Ser Ala Leu
                35                  40                  45

Tyr Arg Glu Ala Leu Glu Ser Pro Glu His Cys Ser Pro His His Thr
 50                  55                  60

Ala Leu Arg Gln Ala Ile Leu Cys Trp Gly Glu Leu Met Thr Leu Ala
 65                  70                  75                  80

Thr Trp Val Gly Val Asn Leu Glu Asp Pro Ala Ser Arg Asp Leu Val
                85                  90                  95

Val Ser Tyr Val Asn Thr Asn Met Gly Leu Lys Phe Arg Gln Leu Leu
                100                 105                 110

Trp Phe His Ile Ser Cys Leu Thr Phe Gly Arg Glu Thr Val Ile Glu
                115                 120                 125

Tyr Leu Val Ser Phe Gly Val Trp Ile Arg Thr Pro Pro Ala Tyr Arg
 130                 135                 140

Pro Pro Asn Ala Pro Ile Leu Ser Thr Leu Pro Ala Gly Asp Tyr Cys
145                 150                 155                 160

Cys
```

(2) INFORMATION FOR SEQ ID NO:20:

(i) SEQUENCE CHARACTERISTICS:
        (A) LENGTH: 183 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
                35                  40                  45

Ser Pro His His Thr Ala Leu Arg Gln Ala Ile Leu Cys Trp Gly Glu
 50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asp Thr Asn Met Gly Leu Lys
                85                  90                  95

Phe Arg Gln Leu Leu Trp Phe Met Ile Ser Cys Leu Thr Phe Gly Arg
                100                 105                 110

Glu Thr Val Ile Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
 130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
                180
```

(2) INFORMATION FOR SEQ ID NO:21:

(i) SEQUENCE CHARACTERISTICS:
    (A) LENGTH: 199 amino acids
    (B) TYPE: amino acid
    (C) STRANDEDNESS: single
    (D) TOPOLOGY: linear (xi) SEQUENCE DESCRIPTION: SEQ ID NO:21:

```
Met Ser Lys Leu Cys Leu Gly Trp Leu Trp Gly Met Asp Ile Asp Pro
1               5                   10                  15

Tyr Lys Glu Phe Gly Ala Thr Val Glu Leu Leu Ser Phe Leu Pro Ser
                20                  25                  30

Asp Phe Phe Pro Ser Val Arg Asp Leu Leu Asp Thr Ala Ser Ala Leu
            35                  40                  45

Tyr Arg Glu Ala Leu Glu Ser Pro Glu His Cys Ser Pro His His Thr
    50                  55                  60

Ala Leu Arg Gln Ala Ile Leu Cys Trp Gly Glu Leu Met Thr Leu Ala
65                  70                  75                  80

Thr Trp Val Gly Val Asn Leu Glu Asp Tyr Lys Asp Asp Asp Asp Lys
                85                  90                  95

Ser Arg Asp Leu Val Val Ser Tyr Val Asn Thr Asn Met Gly Leu Lys
                100                 105                 110

Phe Arg Gln Leu Leu Trp Phe His Ile Ser Cys Leu Thr Phe Gly Arg
            115                 120                 125

Glu Thr Val Ile Glu Tyr Leu Val Ser Phe Gly Val Trp Ile Arg Thr
    130                 135                 140

Pro Pro Ala Tyr Arg Pro Pro Asn Ala Pro Ile Leu Ser Thr Leu Pro
145                 150                 155                 160

Glu Thr Thr Val Val Arg Arg Arg Gly Arg Ser Pro Arg Arg Arg Thr
                165                 170                 175

Pro Ser Pro Arg Arg Arg Arg Ser Gln Ser Pro Arg Arg Arg Arg Ser
            180                 185                 190

Gln Ser Arg Glu Ser Gln Cys
            195
```

INHIBITION OF VIRAL REPLICATION

CROSS REFERENCE TO RELATED APPLICATIONS

Under 35 USC 517 119(e)(1), this application claims the benefit of prior U.S. provisional application Ser. No. 60/025,370, filed Sep. 3, 1996.

This invention was supported in part by the U.S. Government under grant numbers CA-35711 and AA-02169 awarded by the National Institutes of Health. The Government has certain rights in the invention.

BACKGROUND OF THE INVENTION

This invention relates to inhibition of animal viral replication.

HBV is the prototypic member of the hepadnavirus family, a group of enveloped DNA viruses that primarily infect the liver. HBV infection in humans may lead to significant liver diseases, including acute liver failure, chronic active hepatitis, liver cirrhosis and hepatocellular carcinoma (HCC) (McLachlan, *Molecular Biology of the Hepatitis B Virus*, CRC Press, Boca Raton, Fla., 1991). The HBV genome consists of a partially double-stranded 3.2 kb DNA molecule with a relaxed circular conformation. Sequence analysis of the genome reveals that HBV encodes four partially overlapping open reading frames (ORF) that direct the synthesis of at least seven viral gene products. This expansion of coding capacity is due to the presence of multiple in-frame initiation codons within the precore/core and envelope ORFs generating proteins of different lengths that share a common carboxyl terminus but have different amino terminal regions. This phenomenon is exemplified by the precore/core ORF. The genomic promoter of HBV directs the synthesis of two types of 3.5 kb transcripts that differ at their 5' initiation sites. The shorter transcript initiates 5 nucleotides downstream from the precore initiation codon (Will et al., J. Virol. 61:904–911, 1987).

It serves as the messenger RNA (mRNA) for the 21 kDa core protein and the polymerase (Chang et al., Proc. Natl. Acad. Sci. U.S.A. 87:5158–5162, 1990). Following encapsidation into the viral nucleocapsid, this mRNA species acts as the template for reverse transcription to generate viral DNA (Bartenschlager and Schaller, EMBO J. 11:3413–3420 1992; Hirsch et al., Nature 344:552–555, 1990). The longer transcript, which has a 5'-end extension, directs the synthesis of the precore gene product but the transcript is not packaged into the viral nucleocapsid (Nassal et al., Cell 63:1357–1363, 1990; Yaginuma et al., Proc. Natl. Acad. Sci. U.S.A. 84:2678–2686, 1987).

The 21 kDa viral core protein (p21) assembles into a 180 subunit nucleocapsid structure (Birnbaum and Nassal, J. Virol. 64:3319–3330, 1990; Gallina et al., J. Virol. 63:4645–4652, 1989). This molecule is also involved in nucleic acid binding and promotes viral replication (Hatton et al., J. Virol. 66:5232–5241, 1992; Nassal, J. Virol. 66:4107–4116, 1992).

Translation of the precore mRNA results in a core related polypeptide designated p25. This precore protein is identical to p21 except that it has a 29 amino acid (aa) amino terminal extension. The first 19 aa's of this extension act as a signal peptide, directing the protein into the secretory pathway of the cell (Bruss and Gerlich, Virology 163:268–275, 1988; Ou et al., Proc. Natl. Acad. Sci. U.S.A. 83:1578–1582, 1987). The 19 aa signal peptide is subsequently cleaved to generate a 22 kDa intermediate protein product (p22) that is either translocated to the endoplasmic reticulum (ER) or released back into the cytoplasm (Garcia et al., J. Cell. Biol. 106:1093–1104, 1988). In the ER, p22 is cleaved in an arginine-rich domain near the carboxyl terminus to create a 17 kDa soluble protein (p17) known as HBeAg, which is then secreted from the cell (McLachlan, *Molecular Biology of the Hepatitis B Virus*, CRC Press, Boca Raton, Fla., 1991). The exact length of p17 is not known, and appears to vary slightly at the carboxyl terminus.

The function of HBeAg in the biology of HBV infection is unknown. HBeAg is found in the serum of HBV-infected individuals, where it generally correlates with high levels of viremia. HBV titers have been found to decrease in serum when there is a detectable anti-HBeAg immune response (McLachlan, *Molecular Biology of the Hepatitis B Virus*, CRC Press, Boca Raton, Fla., 1991). There is evidence to suggest that HBeAg may function as a circulating protein that blocks cytotoxic T cell activity against HBV core-associated epitopes (Milich et al., Proc. Natl. Acad. Sci. U.S.A. 87:6599–6603, 1990). Furthermore, it has been demonstrated that HBeAg determinants are expressed on the surface of infected hepatocytes and present HBeAg/HBcAg epitopes in the context of HLA class I molecules to the host immune system (Schlicht and Schaller, J. Virol. 63:5399–5404, 1989).

However, a functional precore gene appears inessential for viral replication, at least in animals experimentally infected with the related duck hepatitis B virus (DHBV) and woodchuck hepatitis virus (WHV) (Chang et al., J. Virol. 61:3322–3325, 1987; Chen et al., J. Virol. 66:5682–5684, 1992; Schlicht et al., J. Virol. 61:3701–3709, 1987). With respect to the human virus HBV, viral genomes defective in HBeAg synthesis are frequently found in individuals with chronic infection. The most common mutation detected is a TGG to TAG transition that introduces an amber termination signal at codon 28 in the precore ORF. This naturally occurring HBV mutant has been associated with fulminant hepatitis and high levels of viral replication (Carman et al., Hepatology 14:219–222, 1991; Liang et al., N. Engl. J. Med. 324:1705–1709, 1991; Omata et al., N. Engl. J. Med. 324:1699–1704, 1991) as well as with chronic infection (Brunetto et al., Ital. J. Gastroenterol. 21:151–154, 1989; Carman et al., Lancet 2:588–591, 1989; Naoumov et al., Gastroenterology 102:538–543, 1992; Okamoto et al., J. Virol. 64:1298–1303, 1990; Tong et al., Virology 176:596–603, 1990). However, it is still unclear if HBeAg minus HBV genomes are associated with a more severe form of chronic liver disease. In this respect, one study demonstrated that transfection of an HBeAg minus genome into human HCC cells resulted in increased viral replicative forms as compared to wild type HBV (Lamberts et al., J. Virol. 67:3756–3762, 1993).

SUMMARY OF THE INVENTION

Applicants have discovered that viral replication can be inhibited by introducing at the site of viral nucleocapsid assembly (e.g., within an infected cell) a protein which is not the wild type nucleocapsid component but which can be incorporated into the assembling nucleocapsids (i.e., assembled into the structure of the nucleocapsid shell along with the wild type nucleocapsid component). The hybrid nucleocapsids so produced are deficient in encapsidation of the viral nucleic acid and cannot form viable viral particles. Because the virus's own wild type nucleocapsid proteins are shunted into non-viable nucleocapsids, rather than 100% wild type nucleocapsids, trans-dominant inhibition of viral replication results. Animal viruses of which replication can be so inhibited include, but are not limited to, retroviruses (e.g., human immunodeficiency viruses), herpes simplex viruses, and hepadnaviruses (e.g., duck hepatitis B virus, woodchuck hepatitis virus, and human hepatitis B virus). In the case of human hepatitis B virus (HBV), the inhibitory proteins include the HBV precore proteins or certain variants thereof, which can be incorporated into HBV nucleocapsids along with the p21 core protein (the usual nucleocapsid component), and thereby render the nucleocapsids deficient in encapsidating HBV pregenomic RNA. Thus, overexpression of the precore proteins or certain variants thereof (as defined below) leads to trans-dominant inhibition of HBV replication. By "overexpression" is meant a level of expression for a given coding sequence that is significantly higher (e.g., two fold, and preferably ten fold or even a hundred fold) per cell than the per cell level seen with the corresponding wild type coding sequence in the wild type virion during normal infection. The level of expression of a given coding sequence is generally controlled at the transcription level, and depends upon the expression control sequences (e.g., promoter and enhancer) associated with the coding sequence. It is also affected by the copy number of the coding sequence introduced into the cell.

The inhibitory proteins of the invention include (1) the 25 kDa protein (i.e., p25, SEQ ID NO:3) encoded by the full length HBV precore gene; (2) the 22 kDa protein (i.e., p22, SEQ ID NO:2) that results from the elimination of the 19 amino acid leader peptide from the amino terminus of p25; (3) Met-p22 (SEQ ID NO:18), which is p22 with an added methionine at the N-terminus; (4) the 18 kDa protein (i.e., p18, SEQ ID NO:1) that constitutes the 154 amino terminal residues of p22; (5) Met-p18 (SEQ ID NO:17), which is p18 with an added methionine at the N-terminus; (6) Met-p18-Het (SEQ ID NO:19), which is Met-p18 with an added heterologous sequence (SEQ ID NO:15) at the C-terminus; (7) a protein that is less than all of p25 and contains the full sequence of p18; (8) any protein that is at least 80% homologous (preferably 90%, and more preferably 95%) to any of (1) to (7); and (9) a protein that is described by one of (1) to (8) except that it additionally contains (i.e., has inserted at one end or within its sequence) a peptide sequence of at least one amino acid residue, such as a heterologous epitope, at one or both of its termini, or within its sequence. "80% homologous", as used herein, means that the amino acid sequence of the protein of the invention is the same as or shorter than that of the reference protein sequence, and has 80% sequence identity with the reference protein sequence when analyzed by sequence analysis software such as the Wisconsin Package. The 80% limitation further means that the protein cannot be shorter than 80% of the reference protein sequence, and must contain 80% of the residues of the reference protein sequence, in the same order as the reference protein sequence. The relationship of (1) to (6), p21 (core protein) and p17 (HBeAg) is illustrated in FIG. 2.

"Heterologous", as used herein, is defined as of other than HBV origin. A heterologous peptide preferably contains an epitope distinguishable from HBV in an immunoassay. Preferably, the heterologous peptide consists of a known epitope of 4–14 amino acid residues, or a double or triple concatemer of such an epitope. The heterologous peptide can total up to 50 residues at the amino or carboxyl terminus, or up to 25 residues within the protein, and can replace 0–25 residues of the natural sequence. Examples of such epitopes include FLAG™ (SEQ ID NO:4), E-tag (SEQ ID NO:7), c-myc tag (SEQ ID NO:8), VSV-GP (SEQ ID NO:9), T7-tag (SEQ ID NO:10), HSV-tag (SEQ ID NO:11), and HA tag (SEQ ID NO:12).

Accordingly, HBV replication can be inhibited in a cell by introducing into the cell an effective amount of the inhibitory protein of the invention. This can be accomplished either directly, using a preparation of the protein, or indirectly, by introducing an appropriate expression construct into the cell. The protein preparation can be administered to a target cell, preferably a human hepatocyte, in vivo or ex vivo, in a carrier such as saline and/or liposomes. The administered amount of the preparation should be adequate to ensure that the majority of, and preferably nearly all, HBV nucleocapsids produced within the target cell incorporate at least one molecule of the inhibitory protein into the nucleocapsid shell. If desired, the protein may be tagged with a heterologous peptide sequence that is immunogenic. This permits the protein to be specifically detected in an immunoassay, using an antibody specific for the peptide tag. The heterologous peptide sequence can be attached to either end of the protein, or inserted within the protein at a location such as the immunodominant region corresponding to amino acid residues 82–98 of SEQ ID NO:1 or 2, i.e., amino acid residues 72–88 of the core p21 protein (SEQ ID NO:20). A tag insertion within the immunodominant region destroys the naturally occurring epitope(s) in that region, particularly if some of the naturally occurring epitope residues are deleted. This renders the tagged inhibitory protein unrecognizable by antibodies specific for the region, thereby permitting one to distinguish the tagged inhibitory protein from the wild type core protein p21.

In the genetic therapy method of the invention, one would use a nucleic acid construct (e.g., a construct derived from a vector) that directs overexpression of an inhibitory protein of the invention. The sequence encoding the inhibitory protein is operably linked to transcription control sequences that preferably function primarily or exclusively in hepatocytes. Transcription control sequences can include a transcriptional promoter and/or enhancer and sequences which control the termination of transcription. A transcription control sequence is said to be "operably linked" to a coding sequence if the transcription control sequence controls transcription of the coding sequence. Vectors of the invention include, but are not limited to, plasmid vectors and viral vectors, such as those derived from retroviruses, adenoviruses, adeno-associated virus, Sindbis virus, mumps virus, poliovirus, vaccinia virus (e.g., canary pox virus), herpes simplex virus, and SV40. They can be constituted in a therapeutic composition including a pharmaceutically acceptable excipient such as a diluent or carrier.

HBV replication in a cell (e.g., in a hepatocyte in vivo) can be inhibited or prevented by a method involving identifying a patient suspected of being infected with HBV, and administering to the patient the aforementioned recombinant nucleic acid construct. Delivery methods include, but are not limited to, viral infection, receptor-mediated endocytosis, biolistic transfer, and liposome fusion. In addition to such in vivo methods, the nucleic acid construct can be introduced into a cell in vitro or ex vivo.

An inhibitory protein of the invention can be produced in cultured cells (e.g., *E. coli*, insect cells, or mammalian cells) that harbor a recombinant nucleic acid construct capable of directing overexpression of the protein under proper conditions. The recombinant nucleic acid construct should contain a transcription control sequence(s) (e.g., promoter and enhancer) that can function in the host cell and is operably linked to the coding sequence for the protein.

By "isolated DNA" is meant DNA that is free of the genes which, in the naturally-occurring genome of the organism from which the DNA of the invention is derived, flank the sequence that constitutes the DNA of the invention. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "purified protein" is meant that the protein constitutes at least 50% of the dry weight of the protein preparation. By "substantially pure preparation" of a protein is meant a preparation of the protein which is substantially free from the proteins and other naturally occurring organic molecules with which the protein is naturally associated. This typically means that the protein constitutes at least 60% of the dry weight of the preparation. Preferably, the preparation is at least 75%, more preferably at least 90%, and most preferably at least 99%, by weight, the protein. Purity can be measured and/or obtained by any appropriate method, e.g., column chromatography, polyacrylamide gel electrophoresis, or HPLC.

Other features and advantages of the invention will be apparent from the following description, drawings, and claims.

HBV DNA derived from restriction sites AatII (1411) to BspEI (2327) was cloned into the AatII-SmaI sites of pGEM 7 Zf(+), as represented by the dotted line. The core promoter region and precore and core ORF are depicted. The darker areas correspond to DNA exchanged from a naturally occurring HBV mutant carrying the amber termination signal at codon 28 in the precore ORF (*) and point mutations in the core promoter (black dots). Relevant restriction sites used to define the exchanged fragments are indicated.

Figure 1A:
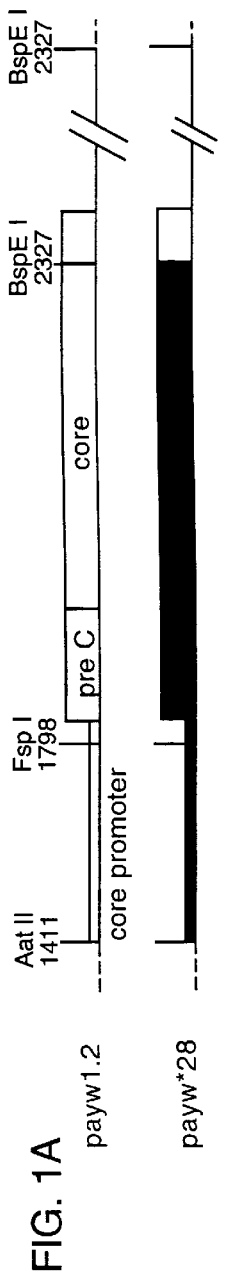
FIG. 1A is a schematic representation of some of the plasmids used in this study. Payw1.2, payw*28, paywFB and paywOM are more-than-one-genome length constructs that express HBV pregenomic RNA from the homologous promoter.
Figure 1B:
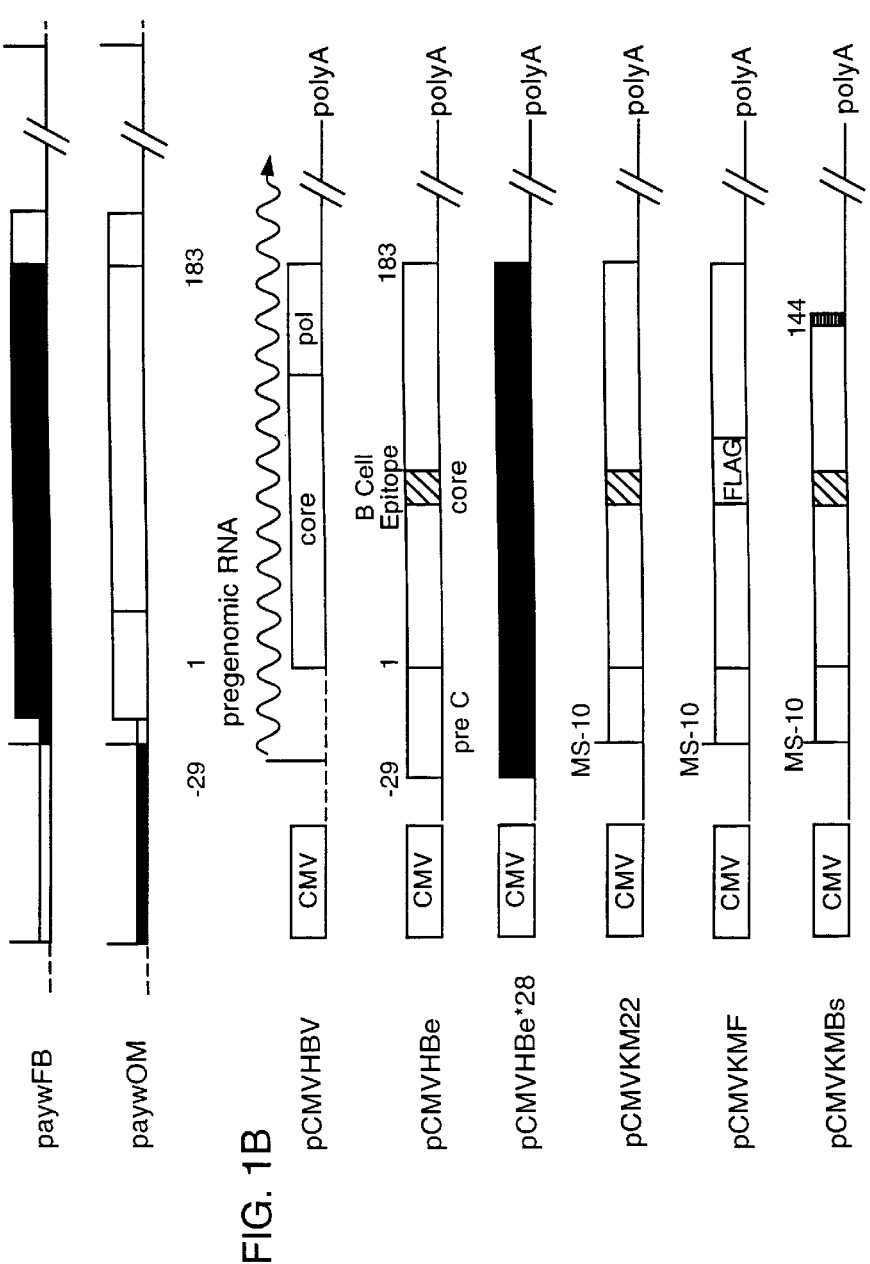

FIG. 1B is a schematic representation of the CMV-promoter-containing plasmids used in this study. pCMVHBV expresses the pregenomic RNA (wavy line). pCMVHBe expresses the entire precore/core ORF. pCMVHBe*28 contains the amber mutation at codon 28 in the precore ORF (*). Position of the first aa in precore ORF is indicated as −29. pCMVKM22 expresses a cDNA with an engineered ATG in front of the codon for serine$^{-10}$ in the precore ORF. The pCMVKMF construct is identical to pCMVKM22 except a FLAG™ epitope has been engineered into the B cell immunodominant loop (hatched area) of the core protein. The pCMVKMBs construct expresses a protein that stops at proline$^{144}$ of the core molecule (SEQ ID NO:20). A polyadenylation signal was provided by the pcDNA3 vector in all plasmids except in pCMVHBV where the polyadenylation site is derived from the endogenous HBV sequence.

Figure 2:
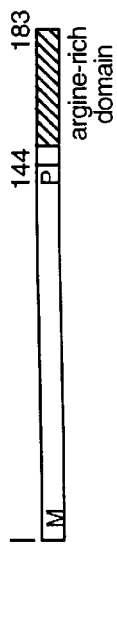
Figure 2:
Figure 2:
Figure 2:
Figure 2:
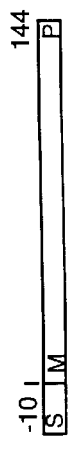
Figure 2:
Figure 2:
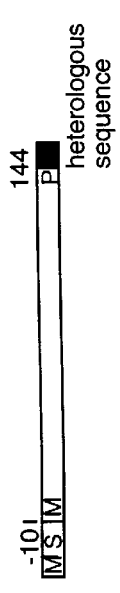
Figure 2:

FIG. 2 is a schematic representation of the aligned polypeptide sequences of p21 (core protein), p25, p22, Met-p22, p18, Met-p18, Met-p18-Het, and p17 (HBeAg). Amino acid numbering corresponds to the precore/core numbering convention, with the start methionine of the core protein (p21) designated position no. 1, and the start methionine of the precore protein (p25) designated −29. "M" stands for methionine residue. "S" stands for serine residue. "P" stands for proline.

DETAILED DESCRIPTION

Described below is evidence that HBV replication is inhibited in the presence of high levels of the HBV precore or precore-related proteins. These inhibitory proteins may be provided exogenously to a target cell in an effective amount which can be determined using routine methodology. This amount will yield an intracellular concentration of the protein significantly higher than that observed for precore proteins during the normal course of HBV infection. Hepatocytes are preferred target cells since they are susceptible to HBV infection. Targeting of the inhibitory proteins to hepatocytes may be achieved by local injection (e.g., into the hepatic portal vein) of liposomes that contain the inhibitory proteins. For enhanced targeting, the liposomes may be coated with molecules which function as ligands of hepatocyte-specific receptors. An example of such a receptor is the hepatic asialoglycoprotein receptor, useful ligands of which include asialo-orosomucoid and (poly)L-lysine-asialo-orosomucoid (Spiess, Biochemistry 29(43):10009–10018, 1990; Wu et al., J. Biol. Chem. 267(18):12436–12439, 1992; Wu et al., Biotherapy 3:87–95, 1991).

Alternatively, the proteins may be introduced into a target cell by overexpressing within the cell a nucleic acid construct comprising a promoter sequence operably linked to a sequence encoding the protein. In this method, the nucleic acid construct is derived from a non-replicating linear or circular DNA or RNA vector, or from an autonomously replicating plasmid or viral vector; or the construct is integrated into the host genome. Any vector that can transfect a hepatocyte may be used in the methods of the invention. Preferred vectors are viral vectors, including those derived from replication-defective hepatitis viruses (e.g., HBV and HCV), retroviruses (see, e.g., WO89/07136; Rosenberg et al., N. Eng. J. Med. 323(9):570–578, 1990), adenovirus (see, e.g., Morsey et al., J. Cell. Biochem., Supp. 17E, 1993), adeno-associated virus (Kotin et al., Proc. Natl. Acad. Sci. USA 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), and any modified versions of these vectors. Methods for constructing expression vectors are well known in the art (see, e.g., *Molecular Cloning: A Laboratory Manual*, Sambrook et al., eds., Cold Spring Harbor Laboratory, 2nd Edition, Cold Spring Harbor, N.Y., 1989).

In these vectors, promoters are operably linked to the nucleic acid sequence encoding the inhibitory protein of the invention. Any promoter that can direct a high level of transcription initiation in hepatocytes may be used in the invention. Non-tissue specific promoters, such as the cytomegalovirus (DeBernardi et al., Proc. Natl. Acad. Sci. U.S.A. 88:9257–9261, 1991, and references therein; Experimental Data), mouse metallothionine I gene (Hammer, et al., J. Mol. Appl. Gen. 1:273–288, 1982), HSV thymidine kinase (McKnight, Cell 31:355–365, 1982), and SV40 early (Benoist et al., Nature 290:304–310, 1981) promoters may be used in the invention, as overexpression of the inhibitory proteins of the invention does not adversely affect transfected cells. However, preferred in the invention are hepatocyte-specific promoters, the use of which ensures that the proteins are expressed primarily in hepatocytes. Hepatocyte-specific promoters include, but are not limited to, the albumin, alpha-fetoprotein, alpha-1-antitrypsin, retinol-binding protein, and asialoglycoprotein receptor promoters. Viral promoters and enhancers that include those derived from herpes simplex viruses (types I and II), hepatitis viruses (A, B, and C), and Rous sarcoma virus (RSV; Fang et al., Hepatology 10:781–787, 1989) may also be used in the invention.

The above-described nucleic acid constructs and vectors can be introduced into target cells as naked DNA, or by liposome fusion, erythrocyte ghosts, or microsphere methods (microparticles; see, e.g., U.S. Pat. No. 4,789,734; U.S. Patent No. 4,925,673; U.S. Pat. No. 3,625,214; Gregoriadis, *Drug Carriers in Biology and Medicine*, pp. 287–341, Academic Press, 1979), Alternatively, the nucleic acid constructs can be coupled to ligands of hepatocyte-specific receptors, and thereby enter hepatocytes via receptor-mediated endocytosis. For example, one could use a ligand which binds the hepatic asialoglycoprotein receptor, such as asialo-oromucoid or (poly)L-lysine-asialo-orosomucoid. Alternatively, one can employ a viral-based vector as a means for introducing the nucleic acid into hepatocytes.

The inhibitory proteins of the invention can be produced in commercially significant amounts by recombinant methods employing cultured cells. The cells can be prokaryotes (e.g., *E. coli*), eukaryotes (e.g., yeast, insect cells, or mammalian cells). The nucleic acid molecules encoding the inhibitory proteins and having appropriate expression control sequences can be introduced into the cultured cells by viral infection, receptor-mediated endocytosis, liposome fusion, or any other standard transfection technique. These cultured cells are particularly useful for producing recombinant inhibitory proteins encoded by the nucleic acid molecules they harbor. Extraction and purification of recombinant proteins produced by tissue culture cells can be performed with techniques well known in the art, including, for example, immunoaffinity purification.

Therapeutic compositions comprising the inhibitory proteins or nucleic acid molecules encoding these proteins can be administered to a hepatitis B patient, or prophylactically to a patient who has not yet shown symptoms of hepatitis B. The therapeutic compositions of the invention may be used alone or in a mixture, or in chemical combination, with one or more materials, including other proteins or recombinant vectors that increase the biological stability of the proteins or the recombinant vectors, or with materials that increase the therapeutic compositions' ability to penetrate hepatocytes selectively. The therapeutic compositions of the invention may be administered in a pharmaceutically acceptable carrier (e.g., physiological saline), which is selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention can be administered in dosages determined to be appropriate by one skilled in the art. An appropriate dosage is one which effects a reduction in the disease caused by HBV infection, which reduces the rate of HBV replication in the patient, and/or which is effective at preventing HBV infection. It is expected that the dosages will vary, depending upon the pharmacokinetic and pharmacodynamic characteristics of the particular agent, and its mode and route of administration, as well as the age, weight, and health (including renal and hepatic function) of the recipient; the nature and extent of the disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, and preferably 1 to 10 mg of active ingredient (nucleic acid or protein) per kilogram of body weight per day, given in divided doses or in sustained release form, is appropriate.

The therapeutic compositions of the invention may be administered to a patient by any appropriate mode, e.g., parenterally, intraperitoneally, or intravenously, as determined by one skilled in the art. Alternatively, it may be desired to administer the treatment surgically to the target tissue. For a patient whose chronically infected liver is removed and replaced with a transplanted liver, the transplant can first be treated ex vivo with the construct of the invention (e.g., by perfusion) to ensure that residual HBV in the patient which infects the new liver will not be able to replicate in the new liver. The treatments of the invention may be repeated as needed, as determined by one skilled in the art.

Experemential Data
Material and Methods
Plasmid Constructs

The plasmid vectors utilized in this study are depicted in FIG. 1. The plasmids payw1.2 and pCMVHBV express HBV pregenomic RNA under the endogenous and the CMV IE promoters, respectively. These two vectors allow HBV replication to occur in HCC cells and cells of non-hepatic origin (Fallows et al., J. Virol. 69:2067–3073, 1995; Seeger et al., J. Virol. 63:4665–4669, 1989). The payw1.2 construct contains more-than-one-genome length of HBV (Galibert et al., Nature 281:646–650, 1979) and carries the genomic fragment between the AatII (nt. position 1411, where nt. 1 is by convention located at the unique GAATT<u>C</u> EcoRI site) and the BspEI sites (nt. 2327). The 3' end BspEI site was blunted by the Klenow DNA polymerase I to allow the cloning of the genomic fragment into the AatII and SmaI restriction sites of the pGEM7 Zf (+) vector (Promega Corporation, Madison, Wisc.).

The plasmid payw*28 has a 0.9 kb AatII-BspEI fragment derived from the plasmid pC*28 (Tong et al., Virology 191:237–245, 1992). This construct carries the nonsense TGG to TAG mutation that introduces a stop codon in the precore ORF at codon 28. This mutant DNA fragment also carries 14 other nucleotide substitutions in the precore/core ORF. In particular, it carries the sequence ATGAT (AAGGT in wild type ayw) that has been found in naturally occurring HBV mutants either alone or in combination with the stop codon 28 mutation in the precore ORF (Okamoto et al., J. Virol. 68:8102–8110, 1994). Exchanging the fragment FspI (1798)—BspEI (2327) in payw1.2 generated plasmid paywFB that contains a stop codon at position 28 in the precore ORF. The counterpart construct paywOM contains the fragment AatII-FspI from pC*28, and therefore has the sequence ATGAT (1759–1763) but lacks the stop codon at position 28 in the precore ORF.

The plasmid pCMVHBe expresses the precore ORF under the control of the CMV IE promoter. The precore ORF was obtained from the plasmid paywSP2, which harbors a deletion in the payw1.2 genome between nt. 2471 and nt. 486. This deletion ablates the HBV preS1, preS2 and a large portion of the HBV polymerase genes, but leaves the precore/core ORF intact. The paywSP2 derived FspI (nt 1798)—SpeI (nt.677) fragment was cloned into the EcoRV—XbaI sites of the pcDNA3 expression vector (Invitrogen Co., San Diego, Calif.). Plasmid pCMVHBe*28, which contains, in the same unit, a stop codon at position 28 in the precore/core ORF, served as a control. To make this construct, a plasmid designated paywSP2*28 was generated by inserting into the backbone of paywSP2 the 0.9 kb AatII—BspEI fragment obtained from pC*28. Subsequently, the FspI—SpeI fragment of paywSP2*28 was subcloned into the EcoRV—XbaI sites of pcDNA3. This vector does not allow the synthesis of either p25 precore or p21 core protein, as shown by in vitro translation experiments in a wheat germ extract system.

Plasmid pCMVKM22 expresses Met-p22 (SEQ ID NO:18), the precore protein lacking the signal peptide sequence and having instead an initial methionine, under the control of the CMV IE promoter. The term p22 is herein (in Experimental Data only) used to denote both the naturally occurring p22 (i.e., without the added methionine) and Met-p22. The coding sequence was modified by PCR amplification using the following two primers: (1) KM22 as a sense primer (5' CGG GGTACCATGTCCAAGCTGTGCCTTGGGTG 3'; SEQ ID NO:13) that introduced a KpnI restriction site (underlined) upstream from an artificial ATG codon (bold); and (2) SP6 as the antisense primer. The DNA template was a SmaI linearized pCMVHBe plasmid. After 25 cycles of PCR amplification—each cycle consisting of 1 min at 95° C., 1 min at 40° C., and 1 min at 72° C.—in the presence of 10 mM Tris-HCl, pH 8.3; 50 mM KCl; 200 µM dNTPs; 2 mM $MgCl_2$; 50 pM of each primer and 2.5 U of Taq DNA polymerase/100 µl of reaction mixture (Roche Molecular Systems, Inc., Branchburgh, N.J.), the amplified DNA was digested by KpnI and ApaI restriction enzymes and cloned into the unique KpnI—ApaI sites in the pcDNA3 polylinker. pCMVKM22 directs the synthesis of a protein that has serine-[10] as the second aa of the Met-p22 precore protein.

pCMVKMBs, a version of pCMVKM22 encoding a polypeptide that is truncated at the carboxyl terminus, was generated as follows. pCMVKM22 was first digested with BspeI, and the staggered ends were subsequently filled in by Klenow DNA polymerase I prior to recircularization of the plasmid. Expression of pCMVKMBs generates a protein of 18 kDa; the aa sequence following the core proline[144] (in reference to the core methionine[1]), is AlaGlyAspTyrCysCysAmber (SEQ ID NO:15). To distinguish during immunoprecipitation the wild type p21 core protein and the p22 synthesized by pCMVKM22, pCMVKMF was generated on the basis of pCMVKM22. pCMVKMF contained an in-frame FLAG™ epitope (Eastman Kodak Co., New Haven, Conn.) that was introduced into the B cell epitope loop corresponding to the core (SEQ ID NO:20) aa residues 75–84 (Standring, *Molecular Biology of the Hepatitis B Virus*, CRC Press, Boca Raton, Fla. 1991) of the core protein, substituting for the wild type core aa residues 79–80. This modification was accomplished by PCR with (1) a reverse primer containing a XbaI site, the FLAG™ sequence, and the HBV-specific sequence (5' GCTCTAGACTTGTCATCGTCGTCCTTGTAATCT-TCCAAATTAACACCCACCCAGG 3'; SEQ ID NO:14), and (2) the above described KM22 sense primer. The DNA template was a SmaI linearized pCMVKM22 plasmid and the PCR reaction was carried out as described above. The PCR product was digested with XbaI and the 166 bp fragment was gel purified and cloned into XbaI digested pCMVKM22.

The retroviral pBabepuro vector (Morgenstein and Land, Nucleic Acids Res. 18:3587–3596, 1990) was used to express the precore ORF under the transcriptional control of the retroviral long terminal repeat. For this purpose, the pcDNAHBe plasmid was digested with BamHI, which cuts 5' to the precore cDNA start in the pcDNAHBe polylinker and again at nt. position 486 in the ayw genome. The BamHI insert was then cloned into the BamHI site of the pBabepuro polylinker, and the construct with the correct insert orientation was designated pBPHBe. The plasmid pCMV Luc (+) was utilized to monitor the transfection efficiency in HCC cells. This plasmid is generated by inserting the firefly luciferase gene into pcDNA3, with expression of the luciferase gene under the control of the CMV IE promoter in the pcDNA vector.

The correct design of the plasmids was ascertained by restriction digest mapping and by direct DNA sequencing. The restriction enzymes were provided by New England BioLabs, Beverly, Mass. Sequencing reactions were carried out with the Sequenase™ Version 2.0 enzyme (USB, Cleveland, Ohio). Plasmid DNAs were grown in JM1O9 *E. coli* cells and purified by a commercially available kit following the manufacturer's instructions (Wizard Maxiprep™ kit; Promega Co. Madison, Wisc.).

Tissue Culture

The HepG2 and HuH7 cell lines were utilized, since they support the complete viral replication cycle and produce infectious virions subsequent to transient transfection with HBV containing plasmids (Acs et al., Proc. Natl. Acad. Sci. U.S.A. 84:4641–4644, 1987). HEK 293, a highly transfectable cell line derived from human embryo kidney (Graham et al., J. Gen. Virol. 36:59–74, 1977), was also utilized, since it efficiently supports viral replication following transfection with a plasmid expressing the HBV pregenome under the control of CMV IE promoter (pCMVHBV), and, to a lesser extent, with the payw1.2 construct driven by the endogenous viral promoter.

HepG2, HuH7 and HEK 293 cell lines were grown in DMEM supplemented with 10% fetal bovine serum. Ten million cells, seeded in a 10 cm petri dish, were transiently co-transfection by the calcium phosphate method ($CaPO_4$ transfection kit, 5'-3', Inc., Boulder, Colo.) with 10 µg of a construct expressing wild type HBV together with various amounts of the other plasmid constructs. Plasmid pGEM7 Zf(+) was added to keep the final amount of transfected DNA constant. The HepG2215 cell line constitutively produces infectious virions (Sells et al., Proc. Natl. Acad. Sci. U.S.A. 84:1005–1009, 1987). Two pools of cells called HepG2215BP and HepG2215BPHBe were derived from this parental cell line by infection with the parental Babepuro and BabepuroHBe retroviral stocks, respectively (Miller et al., Methods Enzymol. 217:581–599, 1993). Transfection efficiency was monitored by adding 1 µg of the pCMV Luc (+) to the transfection reactions and subjecting approximately 1/100 of the cell lysate to the luciferase assay (Ausubel et al., *Current Protocols in Molecular Biology*, Wiley, N.Y., 1989). After transfection, cells were harvested at days 2, 3, and 5 for RNA, protein and DNA analyses.

Analysis of Viral DNA Replication

HBV DNA replication in the cells subsequent to transient transfection was determined by Southern blot analysis of viral DNA extracted from purified intracellular core particles as described by Pugh et al. (Pugh et al., J. Virol. 62:3513–3516, 1988). The same technique was used to evaluate HBV DNA replication in the HepG2215BP and HepG2215BPHBe cell lines. In these experiments, 5×10⁶ cells were seeded in a 10 cm tissue culture dish. After three days of culture, the cells were harvested, and counted; and the capsid-associated viral DNA was examined as described above. DNA was fractionated by agarose gel electrophoresis (*Molecular Cloning: A Laboratory Manual*, Sambrook et al., eds., Cold Spring Harbor Laboratory, 2nd Edition, Cold Spring Harbor, N.Y., 1989) and transferred onto Hybond™ N+ membrane (Amersham International, Little Chalfont, UK) for Southern blot analysis. HBV DNA was detected by hybridization with a random-primed, $^{32}$P-labeled, full length HBV probe. Prehybridization, hybridization and washings were performed as previously reported (Melegari et al., Virology 199:292–300, 1994).

Detection of Viral Proteins

Human HCC cells transfected with the various expression vectors were lysed at 4° C. by the addition of 500 μl of a mixture containing TNE, 1% Nonidet P-40 (NP40) and protease inhibitors (Boehringer Mannheim Corp., Indianapolis, Ind.). The cell lysates were cleared of nuclei and cellular debris by centrifugation at 10,000×g for 1 min. Cell lysates were mixed with Laemmli sample buffer, boiled for 5 min, and electrophoresed through a 15% SDS-polyacrylamide gel (Protogel, National Diagnostics, Atlanta, Ga.). The separated proteins were then transferred onto Immobilon-PT™ membrane (Millipore Co., Bedford, Mass.) (Harlow and Lane, *Antibodies: A Laboratory Manual*, Cold Spring Harbor, Cold Spring Harbor, N.Y. 1988). HBcAg/HBeAg were detected by a rabbit polyclonal antiserum raised against recombinant core protein (Dako Co., Carpinteria, Calif.) as described (Scaglioni et al., Virology 205:112–120, 1994). The same antibody was used for immunoprecipitation of core nucleocapsids at a 1:250 dilution in TNE, 1% NP40 buffer. The anti-FLAG™ antibody was used for both immunoprecipitation and Western blot analysis. Bound antibody was revealed by a chemiluminescence method utilizing horseradish peroxidase-labeled goat anti-rabbit or anti-mouse IgG antibodies (SuperSignal™, Pierce, Rockford, Ill.). Exposure was performed with NEN Reflection™ film (Dupont Company, Boston, Mass.) for 5–20 seconds. Detection of HBeAg in the supernatant of transfected cells was performed with a radioimmunoassay kit specific for HBeAg (EBK $^{125}$I RIA KIT, Incstar Corporation, Stillwater, Minn.). Measurement of HBsAg in the cell culture supernatants was performed using a radio-immunometric assay as previously described (Melegari et al., Virology 199:292–300, 1994).

Viral Nucleocapsid Isolation

Transiently transfected HEK 293 cells were lysed and 200 μl aliquots of the clarified cell lysates were ultracentrifuged at 500,000×g through 2 ml of a 20% w/v sucrose/TNE cushion for 1 hr at 4° C. using a TLA 100 rotor (Beckman Instruments, Palo Alto, Calif.). Under these conditions, viral core particles are pelleted whereas free core protein and soluble HBeAg remain in the supernatant (Zhou and Standring, J. Virol. 66:3086–3092, 1992). The pelleted material was directly analyzed by Western blot analysis or again subjected to ultracentrifugation on sucrose gradients. The resuspended pellet was layered onto 2ml of a 25–60% sucrose/TNE, 1% NP40 mixture. Gradients were established by ultracentrifugation at 55,000 rpm (corresponding to 200,000×g) with a TLS55 rotor for 1 hr at 4° C. Fifteen 150 μl aliquots were collected and protein concentrated as described (Lingappa et al., J. Cell. Biol. 125:99–111, 1994). The resuspended pellet was electrophoresed through a 15% SDS-PAGE gel followed by Western blot analysis.

Extraction and Analysis of Viral RNA

Total RNA was extracted as described two days after transient transfection (Scaglioni et al., Virology 205:112–120, 1994). Core particles derived from the cytoplasm of transfected cells were immunoprecipitated with anti-core antibodies, and protein A-Sepharose® was added. The precipitate was washed with lysis buffer, and encapsidated viral RNA was extracted as previously described (Roychoury et al., J. Virol. 65:3617–3624, 1991), followed by gel electrophoresis and Northern blot analysis of total and encapsidated viral RNA (Ausubel et al., *Current Protocols in Molecular Biology*, Wiley, New York, 1989).

Generation of Recombinant Retroviral Vectors and Infection of HCC Cell Lines

The plasmids pBabepuro and pBabepuroHBe were used to generate recombinant retroviruses (Miller et al., Methods Enzymol. 217:581–599, 1993). Characterization of the packaging cell lines Bosc 23 (Pear et al., Proc. Natl. Acad. Sci. U.S.A. 90: 8392–8396, 1990) and PA317 (CRL-9078, American Type Culture Collection, Rockville, Md.) as well as the conditions for their maintenance and infection have been described (Miller et al., Methods Enzymol. 217:581–599, 1993; Pear et al., Proc. Natl. Acad. Sci. U.S.A. 90:8392–8396, 1990). Briefly, the pBabepuro and pBabepuroHBe plasmids were transiently transfected into the ecotropic packaging cell line Bosc23. Two days later, the culture supernatant was harvested; after addition of polybrene at a final concentration of 8 μg/ml, the supernatant was used to infect the amphitropic packaging cell line PA317. Two days after infection, 2 μg/ml of puromycin was added to the culture medium. The medium derived from drug resistant cells contains recombinant amphitropic retroviruses; PA317 cells infected with pBabepuroHBe were shown to have HBeAg in the supernatant as well. Viral titers were measured as described (Ausubel et al., *Current Protocols in Molecular Biology*, Wiley, New York, 1989). HepG2215 cells were infected with 1×10$^6$ CFU/ml of recombinant retrovirus. After 2 weeks of drug selection, pooled puromycin-resistant clones were expanded and designated as HepG2215BP and HepG2215BPHBe, respectively.

RESULTS

A Stop Codon in the Precore ORF Generates a High Replication Viral Phenotype

Increased levels of HBV replication were observed in HCC cells transiently transfected with payw*28 vector, which contains a stop signal at codon 28 in the precore ORF. Southern blot analysis of purified HBV core particles demonstrated that transfection with payw*28 alone produced a several fold increase in HBV DNA replicative forms as compared to transfection with the wild type payw1.2 construct. The difference between the two plasmids resides only in mutations present in the precore promoter and precore ORF of payw*28. To analyze further the specific mutation(s) responsible for the observed phenotype, a selected DNA fragment was cassette exchanged into the parental payw1.2, yielding paywFB. This paywFB construct carries an amber mutation at codon 28 of the precore ORF and exhibits a high replication phenotype comparable to that of the mutant payw*28 genome. The paywOM, a construct that carries a two nucleotide substitution in a putative transcription-factor-binding site of the precore promoter region (Zhang and McLachlan, Virology 202:430–440, 1994), has a wild type level of HBV replication. To ascertain whether the difference in HBV replicative pattern was related to the cell type used for transfection, experiments were performed in both HepG2 and HuH7 HCC cell lines. Similar results were obtained.

p25 Precore Protein Expression Inhibits HBV Replication

Next, the effect of the precore gene product on HBV replication was evaluated. The wild type payw1.2 HBV-expressing construct was co-transfected with pCMVHBe, a plasmid overexpressing the full length precore protein p25. Under these conditions there was a striking reduction of the wild type HBV replication. In contrast, this level of wild type HBV DNA replication was not affected when the payw1.2 construct was co-transfected with pCMVHBe*28, a plasmid incapable of producing either the precore or the core protein. The same degree of inhibition in HBV replication was observed when pCMVHBV was co-transfected with pCMVHBe. The pCMVHBV construct expresses the pregenomic RNA but does not express a precore transcript (as evidenced by the absence of HBeAg in supernatant derived from transfected cells), since the transcription initiation site is positioned downstream from the CMV IE promoter. Similar results were found when the experiments were repeated. These experiments suggest that the lack of a functional precore gene results in enhanced HBV replication, and that expression of the HBV precore gene product results in striking inhibition of HBV DNA replication.

Precore gene overexpression did not appear to have any adverse effect on transfected cells at the plasmid concentrations used in this study. The HCC cells were routinely analyzed by light microscopy and no evidence of cytotoxicity was observed. Further experiments were conducted to evaluate whether HBV precore gene expression would negatively influence the activity of a panel of transcriptional elements that control the expression of the firefly luciferase gene from the pcDNA3 construct [pCMV Luc (+)]. These transcriptional elements include the HBV precore promoter/Enhancer 1, HBV core promoter, API responsive elements, RSV LTR, SV40 promoter/enhancer and CMV IE promoter. The experiments revealed that these elements were not significantly influenced by co-transfection of pCMVHBe at a DNA molar ratio varying from 20:1 to 1:1.

Inhibition of HBV Replication in HepG2215 Cells by a Retrovirus Expressing the Precore Protein p25

It was of interest to determine if expression of the precore ORF in a different experimental system would also inhibit HBV replication. Replication of HBV DNA was substantially reduced in HepG2215BPHBe cells compared to empty retroviral vector infected HepG2215BP cells. Densitometric scanning analysis indicated that the HBV DNA content of these cells was reduced by at least 90%, compared to the mock virus infected cells. HBsAg levels in the cell culture supernatants were similar to those found in the parental HepG2215 cell line. Finally, the retroviral infected HepG2215 cells appeared identical to the non-infected parental cell line with respect to growth rate and cellular morphology.

Overexpression of the HBV Precore Gene Leads to Alteration of the Nucleocapsid Structure It is possible that the p25 precore protein acted as a dominant negative factor in the nucleocapsid assembly process, as has been observed with a mutant core-surface envelope protein (Scaglioni et al., Virology 205:112–120, 1994). Thus, the capsid structure formed in cells transfected with (a) pCMVHBV alone, (b) pCMVHBV and pCMVHBe in combination at a 1:1 molar ratio, and (c) pCMVHBe alone was evaluated. A single 21 kDa band corresponding to the wild type HBV core protein was detected in cells transfected with pCMVHBV alone. In cells co-transfected with pCMVHBV and pCMVHBe, not only the 21 kDa band but also a fainter core-immunoreactive band with a slower electrophoretic mobility of about 22 kDa was found. Only p22 core-immunoreactive protein was detected in cells transfected with pCMVHBe alone. No HBV core immunoreactive bands were detected in the lysate derived from the mock DNA transfected cells. The material that was derived from the cell lysate and retained on top of the sucrose cushion was analyzed by Western blot analysis. Neither p21 nor p22 HBV core reactive protein was detected when the protein concentration of the samples was comparable to the lanes loaded with the resuspended pellets. The 17 kDa secreted form (HBeAg) of the precore protein was not detected in the cytoplasm of transfected cells by Western blot analysis.

Expression of the p22 Non-Secreted HBeAg Precursor Protein Inhibits HBV DNA Replication The size of the p22 protein closely resembles the processed, non-secreted HBeAg precursor protein (Garcia et al., J. Cell. Biol. 106:1093–1104, 1988; Nassal and Rieger, J. Virol. 67:4307–4315, 1993; Schlight and Wasenauer, J. Virol. 65:6817–6825, 1991; Standring, *Molecular Biology of the Hepatitis B Virus*, CRC Press, Boca Raton, Fla. 1991). Thus, selective expression of this protein was studied with respect to effects on HBV replication. pCMVKM22, which directs the synthesis of a precore-related polypeptide lacking the signal peptide sequence, was employed in the study. HuH7 and HEK 293 cells were transiently transfected with pCMVHBV alone, pCMVHBV and pCMVHBe in combination, or pCMVHBV and pCMVKM22 in combination, and the level of HBV replication was determined. The results obtained from HuH7 and HEK 293 cells were equivalent. While transfection of pCMVHBV in HEK 293 cells resulted in 20 fold higher levels of HBV DNA as compared to HuH7 cells, the pattern of replicative forms was indistinguishable between the two cell lines. Co-transfection with pCMVHBV and pCMVHBe resulted in substantial reduction of viral replication. Strikingly, when pCMVHBV was co-transfected with pCMVKM22, HBV replication was almost completely inhibited. This observation suggests that p22 may be a more potent and direct inhibitor of HBV DNA replication than its immediate p25 precursor protein. Titration experiments were subsequently performed and pCMVHBe was found to inhibit viral DNA synthesis maximally when transfected at a 1:1 molar ratio with pCMVHBV. In contrast, maximal inhibition exhibited by pCMVKM22 was observed at a DNA molar ratio of 1:15 (pCMVKM22:pCMVHBV). Therefore, the pCMVKM22 construct was about 15 fold more potent in inhibiting HBV replication than the pCMVHBe construct.

The pCMVKM22 construct expressed a protein that was found in core-like particles when either transfected alone or in combination with pCMVHBV. Analysis of the pellet derived from cells transfected with these constructs revealed two protein bands of the same intensity. A minor band corresponding in size to the wild type p21 core protein was evident in cells transfected with pCMVKM22. We speculate that this protein may have originated from the use of the second AUG codon of the KM22 mRNA (Nassal, J. Virol. 66:4107–4116, 1992). Analysis of pellets of cells transfected with pCMVHBe alone revealed that the core reactive band migrated slightly faster than the KM22 polypeptide but slower than the wild type p21 core protein. This may result from the methione residue engineered into Met-p22 that would add an extra 130 Da to the polypeptide chain, or the band may represent a partially processed carboxyterminal form of the translocated precore protein (Nassal, J. Virol. 66:4107–4116, 1992; Schlicht and Wasenauer, J. Virol. 65:6817–6825, 1991).

The p22 Protein Inhibits HBV Replication by Interfering With Pregenomic RNA Encapsidation Inhibition of viral replication is believed to be due to the lack of pregenomic RNA encapsidation into the nucleocapsids. To evaluate this possibility, viral RNA was extracted from nucleocapsids immunoprecipitated from HEK 293 cells transfected with pCMVHBV or pCMVKM22 alone, or in combination. Total cytoplasmic and capsid-contained viral RNA was compared by Northern blot analysis. Inside the wild type viral nucleocapsids produced upon transfection with pCMVHBV alone, pregenomic RNA as well as a smear of viral RNA was present, the latter probably due to the RNAse H activity of the viral polymerase. However, encapsidation of 3.5 kb pregenomic RNA was abolished when pCMVKM22 was co-transfected with pCMVHBV. There was no evidence that the pCMVKM22-derived transcript inhibits transcription of the pregenomic RNA. The same type of analysis performed on RNA extracted from PEG-precipitated nucleocapsids revealed similar results.

Comparison of the Relative Inhibitory Activities of Precore Proteins on HBV DNA Replication It was of interest to determine if expression of the precore gene reverses the high replication phenotype exhibited by the payw*28 construct. Southern blot analysis of HCC cells transiently transfected with payw*28 together with increasing amounts of pCMVHBe demonstrated that only 2 μg of pCMVHBe was required to reduce the high level of viral replication exhibited by the mutant payw*28 to wild type HBV levels. Transfection with increasing amounts of pCMVHBe further depressed both payw*28- and wild type payw1.2-generated HBV DNA replicative forms. This inhibitory effect was shown to be dependent on the presence of a functional wild type precore gene, since expression of pCMVHBe*28 does not affect wild type HBV DNA replication.

The relative potency of precore-related proteins with respect to inhibition of HBV DNA replication was examined in the HEK 293 cells, since this system has a high wild type HBV replication capacity. When pCMVHBV was co-transfected along with pCMVHBe, inhibition of viral replication was about 10 times less than that observed when pCMVKM22 or pCMVKMBs replaces pCMVHBe. The pCMVKMBs protein product (Met-p18, or p18 as used in Experimental Data only; SEQ ID NO:17) was capable of exerting the same degree of inhibition on viral replication as the p22 species produced from the parental pCMVKM22 construct. This experiment demonstrates that the domain responsible for the inhibition of viral replication is not located within the arginine-rich carboxyterminal region encoded by the core ORF.

Expression of the p22 Precore Protein Results in the Formation of Hybrid Nucleocapsids Previous experiments demonstrated that p22 protein was found in the pellet either alone or in combination with wild type p21 core after sedimentation through a 20% sucrose cushion. To determine whether p22 had formed hybrid nucleocapsids with p21, the pellet derived from HEK 293 cells transiently transfected with pCMVHBV or pCMVKM22 alone or both together was resuspended, loaded onto a 20% to 60% sucrose gradient, and ultracentrifuged at 200,000×g for 1 hr. Following this sedimentation procedure, fifteen 150 μl fractions were sequentially removed from the top of the gradient and half of each fraction was analyzed by Western blot for the presence of core immunoreactive proteins. Under these experimental conditions, mature core particles were found predominantly in fractions 4 to 10 (Zhou and Standring, J. Virol. 66:3086–3092, 1992).

HEK 293 cells transfected with the wild type HBV expressing construct displayed the expected sedimentation pattern for core protein. The majority of the core polypeptides assembled into native nucleocapsids were found to reside in fractions 4 to 9. When wild type HBV- and p22-expressing constructs were transfected together, p22 co-sedimented in the same fractions as native nucleocapsids. Interestingly, p22 expressed from the pCMVKM22 construct alone also sedimented as particulate nucleocapsids in the same fraction as would be expected for p21-containing nucleocapsids. Indeed, the sedimentation pattern of p22 overlapped with that of the wild type nucleocapsids. These results suggest that hybrid capsid-like particles consisting of p21 and p22 derived core proteins may be assembled in HEK 293 following transient transfection.

Since the p22 protein itself makes nucleocapsids that have the same sedimentation pattern as nucleocapsids made of p21, it was difficult to determine whether p22 can also form hybrid nucleocapsids together with p21. Moreover, p22 and p21 were indistinguishable by available antibodies. Thus, a FLAG™ epitope was introduced into the B cell immunodominant loop of the p22 core protein derived from plasmid pCMVKM22. This pCMVKMF construct expressed a protein pF22 (SEQ ID NO:21) that is identical to Met-p22 (SEQ ID NO:18) except having the sequence $D^{78}YKDDDDK^{81}$ (SEQ ID NO:4; FLAG™ epitope is underlined; the numbering is in reference to the core p21 protein, SEQ ID NO:20) instead of $D^{78}PAS^{81}$ (SEQ ID NO:16). The pF22 protein assembles into nucleocapsid particles as readily as the p22 parental protein. Western blot analysis of the pellet derived from HEK 293 cells transfected with pCMVKMF demonstrated that pF22 was not detectable by polyclonal anti-core antibodies, suggesting that the immunoreactivity of these antibodies was directed against the antigenic loop where the FLAG™ epitope was inserted. When the resuspended pellet derived from cells co-transfected with pCMVHBV and pCMVKMF was immunoprecipitated by the anti-FLAG™ antibody and the immunoprecipitate was analyzed by Western blot analysis with the polyclonal anti-core antibodies, the wild type p21 core protein was detected. Thus, the wild type p21 core and pF22 proteins co-immunoprecipitate, suggesting that the two polypeptide species physically interact. Taken together with the sedimentation properties of p21 and p22, the results indicate that p22 and p21 can assemble to form hybrid nucleocapsids.

The p18 protein expressed from pCMVKMBs traverses poorly through the sucrose cushion. This finding is in agreement with previous studies demonstrating that a core protein truncated upstream from aa 144 results in formation of a less stable nucleocapsid structure (Birnbaum and Nassal, J. Virol. 64:3319–3330, 1990; Gallina et al., J. Virol. 63:4645–4652, 1989). When this expression vector was co-transfected with pCMVHBV, p18 was detected at a much higher level in the pelleted material together with the wild type p21 core protein. Thus, although partially deficient with respect to self-assembly into nucleocapsids in the absence of p21, p18 was still capable of being incorporated into nucleocapsids along with p21. As discussed above, these p18/p21 hybrid nucleocapsids inhibit HBV replication. The heterologous sequence (SEQ ID NO:15) at the C terminus of p18 (or Met-p18-Het as used in the following claims) does not detract from the inhibitory activity of p18.

Other Embodiments

From the above description, one skilled in the art can easily ascertain the essential characteristics of the present invention, and without departing from the spirit and scope thereof, can make various changes and modifications of the invention to adapt it to various usages and conditions.

All publications cited herein are fully incorporated by reference herein in their entirety. Other embodiments are in the claims set forth below.

We claim:

1. An isolated DNA molecule that encodes a polypeptide consisting of the amino acid sequence set forth as SEQ ID NO:1, SEQ ID NO:17, or SEQ ID NO:19, wherein said polypeptide can be incorporated along with wild type nucleocapsid subunits into an HBV nucleocapsid, thereby rendering the nucleocapsid deficient in encapsidating HBV pregenomic RNA.

2. An isolated DNA molecule that encodes a polypeptide consisting of the amino acid sequence set forth as SEQ ID NO:1, SEQ ID NO:17, or SEQ ID NO:19 into which has been inserted a heterologous peptide sequence 4–25 amino acid residues in length, said peptide sequence replacing 0–25 contiguous amino acid residues of SEQ ID NO:1, SEQ ID NO:17, or SEQ ID NO:19.

3. The DNA molecule of claim 2, wherein said polypeptide consists of the amino acid sequence set forth as SEQ ID NO:1 into which has been inserted said heterologous peptide sequence within a region corresponding to amino acid residues 82–98 of SEQ ID NO:1.

4. An isolated DNA molecule that encodes a polypeptide consisting of the amino acid sequence set forth as SEQ ID NO:1, SEQ ID NO:17, or SEQ ID NO:19 into which has been inserted a heterologous peptide sequence 4–25 amino acid residues in length, said peptide sequence replacing 0–25 contiguous amino acid residues of SEQ ID NO:1, SEQ ID NO:17, or SEQ ID NO:19, and wherein said polypeptide additionally comprises, at its carboxyl terminus, a sequence consisting of one or more contiguous amino acid residues of SEQ ID NO:5.

5. An isolated DNA molecule that encodes a polypeptide consisting of the amino acid sequence set forth as SEQ ID NO:1, SEQ ID NO:17, or SEQ ID NO:19 into which has been inserted a heterologous peptide sequence 4–25 amino acid residues in length, said peptide sequence replacing 0–25 contiguous amino acid residues of SEQ ID NO:1, SEQ ID NO:17, or SEQ ID NO:19, and wherein said polypeptide additionally comprises, at its carboxyl terminus, a sequence consisting of one or more contiguous amino acid residues of SEQ ID NO:6.

6. An isolated DNA molecule that encodes a polypeptide consisting of the amino acid sequence set forth as SEQ ID NO:2, wherein said polypeptide can be incorporated along with wild type nucleocapsid subunits into an HBV nucleocapsid, thereby rendering the nucleocapsid deficient in encapsidating HBV pregenomic RNA.

7. An isolated DNA molecule that encodes a polypeptide consisting of the amino acid sequence set forth as SEQ ID NO:2 or SEQ ID NO:18 into which has been inserted a heterologous peptide sequence 4–25 amino acid residues in length, said peptide sequence replacing 0–25 contiguous amino acid residues of SEQ ID NO:2 or SEQ ID NO:18.

8. An isolated DNA molecule that encodes a polypeptide consisting of the amino acid sequence set forth as SEQ ID NO:2 or SEQ ID NO:18 into which has been inserted a heterologous peptide sequence 4–25 amino acid residues in length, said peptide sequence replacing 0–25 contiguous amino acid residues of SEQ ID NO:2 or SEQ ID NO:18 within a region corresponding to amino acid residues 82–98 of SEQ ID NO:2, or residues 83–99 of SEQ ID NO:18.

9. The DNA molecule of claim 8, wherein the amino acid sequence of said protein consists of (a) SEQ ID NO:2 of which residues 89 and 90 are deleted and replaced with the sequence consisting of SEQ ID NO:4; or (b) SEQ ID NO:18 of which residues 90 and 91 are deleted and replaced with the sequence consisting of SEQ ID NO:4.

10. An isolated DNA molecule that encodes a polypeptide consisting of the amino acid sequence set forth as SEQ ID NO:2 or SEQ ID NO:18 into which has been inserted a heterologous peptide sequence 4–25 amino acid residues in length, said peptide sequence replacing 0–25 contiguous amino acid residues of SEQ ID NO:2 or SEQ ID NO:18, wherein the sequence of said peptide is selected from the group consisting of SEQ ID NOs: 4, 7, 8, 9, 10, 11, and 12.

* * * * *